United States Patent [19]
Saltzman

[11] 3,941,563
[45] Mar. 2, 1976

[54] METHOD AND APPARATUS FOR DETECTING HEXAVALENT CHROMIUM

[75] Inventor: Robert S. Saltzman, Wilmington, Del.

[73] Assignee: E. I. Du Pont de Nemours & Company, Wilmington, Del.

[22] Filed: Apr. 23, 1974

[21] Appl. No.: 463,309

[52] U.S. Cl. ............ 23/230 R; 23/253 R; 356/36
[51] Int. Cl.² ............... G01N 33/18; G01N 21/26
[58] Field of Search .......... 356/36; 23/253 R, 230 R

[56] References Cited
UNITED STATES PATENTS

| | | |
|---|---|---|
| 3,341,299 | 9/1967 | Catravas ............... 23/253 X |
| 3,415,627 | 12/1968 | Rait ....................... 23/253 R |
| 3,572,994 | 3/1971 | Hochstrasser ......... 23/253 X |
| 3,704,953 | 12/1972 | Carter et al. .......... 23/253 X |
| 3,713,776 | 1/1973 | Capuano ................ 23/253 R |

Primary Examiner—R. E. Serwin

[57] ABSTRACT

Disclosed herein is a process and apparatus for quantitatively determining the amount of hexavalent chromium ($CR^{+6}$) in a process stream by comparing the optical density of the process stream with a reference sample produced by reducing $Cr^{+6}$ to $Cr^{+3}$ by contacting it with a sulfur dioxide reducing agent.

9 Claims, 2 Drawing Figures

3,941,563

METHOD AND APPARATUS FOR DETECTING HEXAVALENT CHROMIUM

BACKGROUND OF THE INVENTION

1. Field of the Invention

This invention relates to a process and apparatus for quantitatively determining the amount of hexavalent chromium ($Cr^{+6}$) in a process stream. In particular, it relates to a process and apparatus for measuring small quantities of $CR^{+6}$ in process streams containing a variety of other interfering components.

2. Discussion of the Prior Art

Hexavalent chromium has been listed by the Environmental Protection Agency (EPA) as one of the primary pollutants which must be controlled and monitored in waste water streams. A concentration limit of 0.05 ppm of hexavalent chromium in such streams has been proposed.

The standard method used to detect $Cr^{+6}$ is to react $Cr^{+6}$ with diphenylcarbazide to produce a reddish purple color in slightly acid solutions. This procedure, however, is not easily adapted to a continuous measurement.

Hexavalent chromium ($Cr^{+6}$) absorbs strongly in the near ultraviolet (UV). Its presence in large concentrations, is therefore easily detected by UV spectroscopy. Its presence in small concentrations is also easily detected by UV spectroscopy, provided that there are no other impurities in the medium which would mask the presence of $Cr^{+6}$. Direct photometric absorption measurements for $Cr^{+6}$ in the part per billion/part per million range in plant effluent waters, however, have not been used because the varying absorption of other impurities in the water usually exceeds that of the $Cr^{+6}$.

There is a need, therefore, for a simple, accurate technique to continuously monitor process streams for the presence of $Cr^{+6}$ in amounts commensurate with EPA levels.

The present invention uses a sulfur dioxide reducing agent, preferably sulfur dioxide gas, to reduce $Cr^{+6}$ to trivalent chromium ($Cr^{+3}$) and provide a reference sample to compensate for background absorption. $SO_2$ gas has been used for the abatement of chromium in plant effluent waters, by reducing $Cr^{+6}$ to $Cr^{+3}$ and then precipitating $Cr^{+3}$ by making the stream basic. However, $SO_2$ has never been used in the analysis of a process stream for $Cr^{+6}$; nor has it been used to produce a reference sample from a plant stream which can, in turn, be used to provide an accurate determination of the $Cr^{+6}$ content of that stream. It is the use of $SO_2$ to produce a reference sample which makes such an accurate determination possible, and it is not readily apparent, from the use of $SO_2$ in abatement procedures, that such a reference sample will permit accurate measurements of the $Cr^{+6}$ content in process streams, particularly when that stream contains small concentrations (in the ppm range) of $Cr^{+6}$ in combination with high concentrations of other interfering materials.

SUMMARY OF THE INVENTION

The present invention provides a simple, accurate process for quantitatively determining small amounts of $Cr^{+6}$ in at least one process stream by:

a. monitoring the absorbance of at least a portion of the process stream;

b. introducing a sulfur dioxide reducing agent into at least a portion of the process stream to form a reference sample; and c. after a time sufficient to allow the sulfur oxide containing reducing agent to reduce $Cr^{+6}$ to $Cr^{+3}$, measuring the difference in absorbance of the process stream and the reference sample.

As used in this specification, the term sulfur dioxide reducing agent shall include sulfur dioxide itself ($SO_2$), particularly in its gaseous form, sulfurous acid ($H_2SO_3$) which is a solution of sulfur dioxide in water, and the salts of sulfurous acid, particularly the bisulfites such as sodium bisulfite ($NaHSO_3$). Because of its ease of use, sulfur dioxide gas is the preferred form, and, for convenience, all further discussions in this specification will be limited to the use of sulfur dioxide gas in the practice of the present invention. However, when sulfur dioxide gas is introduced into an acidic aqueous solution, sulfurous acid is formed and when it is introduced into a slightly basic solution, bisulfites are formed. In particular, where sulfur dioxide gas is added to a solution which has been made basic by adding sodium hydroxide (NaOH), sodium bisulfite will be formed. Therefore, even when sulfur dioxide gas is used, either sulfurous acid or a bisulfite will be present in the process stream, depending on the pH of the stream. Although the following discussion will be limited to the use of sulfur dioxide gas, it is to be understood that if the circumstances warrant it, rather than use sulfur dioxide gas, sulfurous acid or a bisulfite solution can be added directly to the process stream. In this case the source of reducing agent would be a liquid under pressure, rather than a gas under pressure.

Also, as used in this specification, the term absorbance shall mean either the actual absorbance of the medium referred to, or a quantity related to the absorbance of the medium, such as the optical density or the light transmittance of the medium referred to.

In the preferred embodiment, a portion of the process stream is first isolated to form a sample stream and the steps referred to above are performed on the sample stream. $SO_2$ can be introduced periodically into the sample stream so the step of monitoring the absorbance of the sample stream and measuring the difference in the absorbance of the sample stream and the reference sample can be accomplished at different times at the same location.

It is not necessary that the pH of the system be maintained constant, but since the absorption of $CR^{+6}$ varies with the pH of the medium in which it is found, both the reference and the sample stream should be either always basic or always acidic. If the pH of the process stream varies from basic to acidic, a base or an acid can be added to the stream in sufficient strengths to keep it either always basic or always acidic. It has been found that $Cr^{+6}$ has its strongest absorption in basic solutions, so in a still more preferred embodiment of the present invention, the process further comprises the step of maintaining the pH of the sample stream and the reference sample at a pH above about 10.0. When the pH is maintained basic, best results are obtained by measuring the difference in the absorbance of the sample stream and the reference stream at a wavelength between about 330 and 420 nm., preferably between 350 and 380 nm.

One convenient way to measure the difference in the absorbance of the sample stream and the reference sample is to measure the absorbance of both the sample stream and the reference sample and to use the measured value of the absorbance of the reference sample to provide a "zero" for the measurement of the absorbance of the sample stream. In one such process, the first step would be to introduce $SO_2$ into the sample stream for a first period of time (usually between one and three minutes) to produce the reference sample, and to set the output of the photometer so that it reads "zero" at this point. The flow of $SO_2$ would then be cut off for a second period of time (usually substantially longer than the first period of time). The difference in the absorbance of the reference sample and the sample stream would then be read directly from the output of the photometer.

This measurement would then provide a differential measure of the amount of $Cr^{+6}$ converted to $Cr^{+3}$ by the $SO_2$ and hence a measure of the $Cr^{+6}$ in the process stream. If the analysis is to be performed on a medium with a high background or a highly turbid stream filled with fine bubbles, differential comparison of the differential measurement referred to above with a reference measurement made in a region of the spectrum where $Cr^{+6}$ does not absorb strongly (i.e., about 750 nm.) may be useful The apparatus of the present invention comprises:

a. at least one conduit means to contain the flow of at least a portion of the process stream;

b. photometric means associated with the conduit means to monitor the absorbance of at least a portion of the process stream;

c. valving means associated with the conduit means to introduce $SO_2$ into at least a portion of the process stream in the conduit means to form a reference sample;

d. residence means associated with the conduit means to allow the $SO_2$ to reduce the $Cr^{+6}$ in the reference sample to $CR^{+3}$; and e. a photometric means associated with said conduit means to measure the difference in the absorbance of the process stream and the reference sample.

The apparatus may further comprise means associated with the conduit means to maintain the pH of both the reference stream and the process stream either always basic or always acidic.

In the preferred embodiment, the conduit means comprises a sample stream conduit to isolate a portion of the process stream into a sample stream, and, the various other components of the apparatus are associated with the sample stream conduit. The valving means to introduce $SO_2$ into the sample stream may be a means to periodically introduce $SO_2$ into the sample stream, in which case the photometric means to monitor the absorbance of the process stream and the photometric means to mesure the difference in the absorbance of the sample stream and the reference sample may comprise a single optical cell where both monitoring the absorbance of the sample stream and measuring the difference in the absorbance of the sample stream and the reference sample are accomplished.

If a differential measurement is to be made, the photometric means comprises:

a. means to measure the absorbance of both the sample stream and the reference sample; and b. means to zero the output of the photometric means to the measured value of the absorbance of the reference sample.

BRIEF DESCRIPTION OF THE FIGURES

The present invention can best be described with reference to the following figures in which.

DETAILED DESCRIPTION OF THE PREFERRED EMBODIMENT

Figure 1:
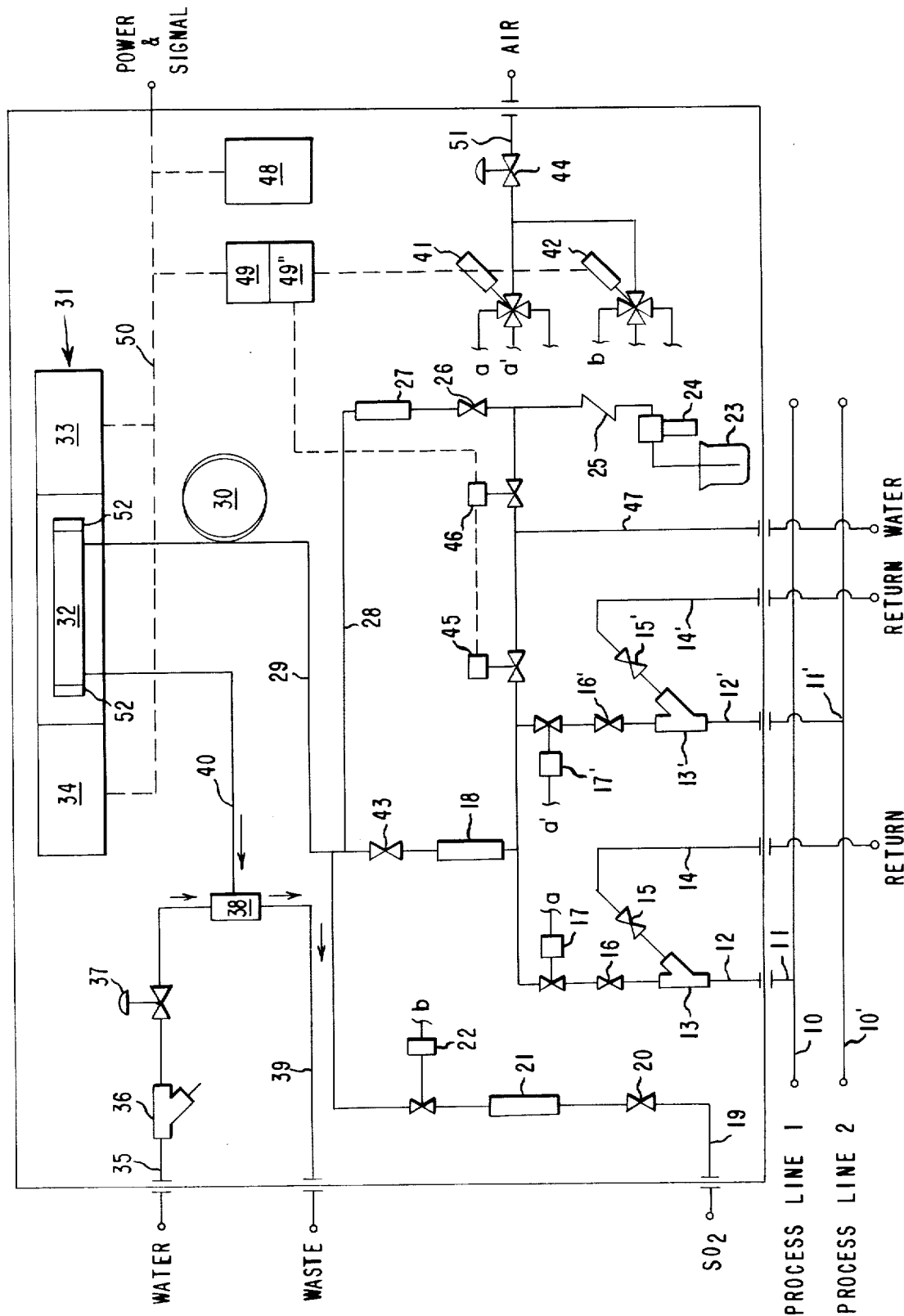
FIG. 1 is a schematic illustration of one embodiment of an apparatus according to the present invention.

FIG. 1 illustrates one embodiment of an apparatus of the present invention which can be used to measure small concentrations of $Cr^{+6}$ in two different process streams. The apparatus illustrated in FIG. 1 can easily be adapted by one skilled in the art for use on a single process stream, or for use on more than two process streams, by deleting the second sample flow system or by adding additional sample flow systems as desired.

In FIG. 1, conduit means 10 and 10' are part of the process lines for two difference process streams. Referring first to process line 1, a tee 11 is provided to isolate a portion of the sample stream conduit 12. Usually the pressure in the process line is sufficient to force a portion of the process stream contained in conduit 10 into sample stream conduit 12, so that no pumping system is necessary to divert a portion of the process stream into the sample system. However, a pump can be provided if necessary. Under certain circumstances, i.e., low process stream flow, the entire process stream can be fed to the sample system and no means to isolate a portion of the process stream into a sample stream is necessary.

The sample stream which has been isolated from the process stream by diverting it to the sample stream conduit 12 passes through a self-cleaning filter 13 which is provided to prevent particles larger than 200 mesh from entering the sample system. A portion of the sample stream diverted from the process stream is then passed to the sample system and a portion of it is diverted into a return line 14 through shut-off valve 15. The undiverted sample stream passes through shut-off valve 16 and a remotely operated ball valve 17 to rotameter 18 which is used to indicate sample flow. All of these parts are standard parts well known to those skilled in the art.

A system identical to that described above is also provided for process line 2.

A valving means, associated with the sample stream conduit, is provided to introduce $SO_2$ into the system. This valving means consists of conduit 19, shut-off valve 20, rotameter 21 (to indicate $SO_2$ flow) and remotely operated ball-valve 22 which is used to periodically introduce $SO_2$ into the sample stream conduit. $SO_2$ gas is provided under pressure to conduit 19. A flow of about 200 cc/min. has been found to be sufficient, but the exact flow will depend on the range of $Cr^{+6}$ to be analyzed.

Additional means, associated with the sample stream conduit, is also provided to maintain the pH of the sample stream at a substantially constant value. As can be seen from FIG. 2, the absorption of $Cr^{+6}$ is increased in a basic solution. Since the sensitivity of the system will be increased if the analysis is conducted in a basic solution, in the embodiment illustrated, the sample contained in the sample stream conduit is maintained at a pH above about 10 by introducing a caustic solution, such as sodium hydroxide (NaOH), into the sample stream conduit. The caustic solution is contained in a container 23. A 25–30% NaOH solution to which is added sodium ethylene diaminetetraacetic acid (EDTA) in the proportion of ½ pound of EDTA to 5 gallons of caustic solution has been found to be suitable. The caustic solution passes through a filter 24 (to remove particulate matter from the caustic solution) and then through check valve 25, shut-off valve 26 and rotameter 27 (which is provided to indicate the flow of caustic solution).

In this manner, $SO_2$, sample stream and caustic solution are combined and introduced into conduit 29. The flow of each component, indicated by the various rotameters, can be controlled by valves 16, 20 and 26. In addition to the materials referred to above, a source of water under pressure is provided through conduit 47 and remotely operated ball-valves 45 and 46. The water is used to purge and clean the system and also to backflush the self-cleaning filters 13 and 13'. Valve 43 is provided to insure that the water is diverted to backflush the filter. Check valve 25 is contained in the caustic solution line to prevent water from reaching the caustic solution.

Caustic solution and sample stream can be provided to the photometer by means of a pump, but in the embodiment illustrated, an aspirator system is used to draw the caustic solution and sample stream through the analysis cell. Water is provided to aspirator 38 through line 35, filter 36 and regulator 37. From the aspirator it is fed to waste line 39. The flow of water through the aspirator provides sufficient suction to draw the caustic solution from its container through line 28 where it is introduced into the sample conduit. The sample stream, caustic solution and $SO_2$ are also drawn through the photometric means 31 into waste lines 39 and 40 by virtue of the suction provided by aspirator 38.

A residence means, which in the embodiment illustrated is a coil 30, is provided in line 29 to provide sufficient residence time for the $SO_2$ in the sample stream to reduce the $Cr^{+6}$ in the sample stream to $Cr^{+3}$ before it is introduced into the photometer. An excess of $SO_2$ is used, and the conversion usually takes less than a few seconds. $SO_2$ dissolves more rapidly in basic solution, so a coil length of about one foot for a basic sample and six feet for an acidic sample is sufficient to provide the residence time necessary.

In the embodiment illustrated, the photometer is a Du Pont 400 Photometric Analyzer containing a sample cell 32 into which the sample stream is introduced through line 29 and removed through line 40. The cell has windows which are transparent to ultraviolet radiation (usually quartz) and is disposed between a light source 33 and a detector 34. The optical features of this instrument are described in U.S. Pat. No. 3,306,156, the disclosure of which is hereby incorporated into this specification.

Figure 2:
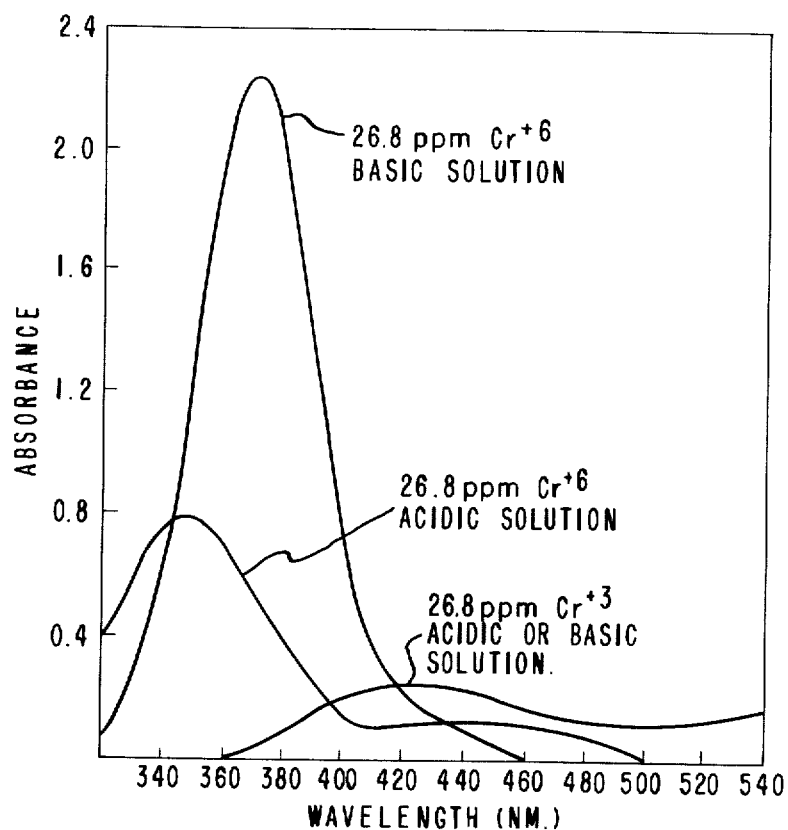
FIG. 2 is a plot of the absorbance of $Cr^{+6}$ in both the basic and acidic solutions compared with the absorption of $Cr^{+3}$ in an acidic or basic solution.

As can be seen from FIG. 2, $Cr^{+6}$ is strongly absorbant in the ultraviolet range between 330 and 420 nm., whereas $Cr^{+3}$ is a weak absorbance in this range. For this reason, the light source is provided with a filter to insure that the analysis takes place in the range 330 to 420 nm., preferably 360 to 380 nm. Analysis at about 365 nm. has been found to be optimum. If differential measurements are to be made of the absorbance of both the sample stream and the reference sample, then a reference wavelength of about 750 nm. may be used.

The light source and detector are powered through lines 50 by a power supply 48. The signal output is zeroed and spanned by a control station 49 which is part of the photometer. Also included in 49 is a sequence controller 49'.

For purposes of the present invention, it is possible to measure the absorbance of the sample stream in one sample cell, and that of the reference sample, produced by introducing $SO_2$ into the sample stream, in a different sample cell. In the embodiment illustrated, however, both the absorbance of the process stream and the absorbance of the reference sample are made using the same sample cell. This is done by allowing the process stream to flow through the photometer sample cell and by periodically introducing $SO_2$ into the sample stream to create a periodic reference sample which also flows through the same photometer sample cell.

The periodic nature of the system is controlled by solenoid valves 41 and 42 which direct the air provided thorugh line 51 and regulator 44, and by solenoid valves 45 and 46. Four way solenoid valve 41 is used to switch from one sample stream to another by operating remote-operated valves 17 and 17'. Solenoid valve 42 is used to operate remote valve 22 in the $So_2$ line and to periodically introduce $SO_2$ into the sample stream at the desired intervals. Solenoid valves 45 and 46 are used to purge the lines with water. All four solenoid valves are controlled by sequence controller 49'' which is programmed to operate the system as desired.

In the embodiment illustrated, the measurement of the absorbance of the reference sample is used to zero the photometer so the output of the photometer when it is used to measure the absorbance of the sample stream will provide a differential measurement proportional to the amount of $Cr^{+6}$ converted to $Cr^{+3}$ by interaction with the $SO_2$. One convenient way in which this can be accomplished is to "zero" the system be bleeding $SO_2$ gas into the sample stream for approximately two minutes during which any $Cr^{+6}$ in the sample stream will be reduced to $Cr^{+3}$. During the last 0.5 minutes of this step, the analyzer is automatically zeroed by conventional electronics provided in sequence controller 49'. Then, for approximately eight minutes, the sample stream is fed unaltered to the analyzer and the amount of $Cr^{+6}$ in the process stream can be determined directly from the output of the analyzer. In the normal sequence, should the source stream contain a high volume of solids, or require caustic addition for pH adjustment, a third step is included in the analysis cycle. For approximately 0.3 minutes, following the $Cr^{+6}$ analysis, the sample and caustic lines are forward flushed and the filters are backflushed to remove contaminants. It should be noted, that if a pH adjustment is required, caustic addition is continuous during both the zeroing and the $Cr^{+6}$ analysis step.

The above description was presented for the purpose of illustrating the invention and is not intended to limit the scope of the invention set forth in the following claims.

What is claimed is:

1. A process for quantitatively determining the amount of $Cr^{+6}$ in at least one process stream comprising the steps of:
   a. monitoring the absorbance of at least a portion of the process stream;
   b. introducing a sulfur dioxide reducing agent into at least a portion of the process stream to form a reference sample; and c. after a time sufficient to allow the sulfur dioxide agent to reduce $Cr^{+6}$ to $Cr^{+3}$, measuring the difference in the absorbance of the process stream and the reference sample.

2. The process of claim 1 wherein the step of introducing a sulfur dioxide reducing agent into the process stream is accomplished by introducing $SO_2$ gas into the process stream.

3. The process of claim 2 wherein the process stream and the reference stream are maintained always basic or always acidic.

4. The process of claim 3 comprising the step of first isolating a portion of said process stream to form a sample stream and then performing the remaining process steps on said sample stream.

5. The process of claim 4 wherein the step of measuring the difference in the absorbance of the sample stream and the reference sample is accomplished by measuring the absorbance of both the sample stream and the reference sample and zeroing the measurement made on the sample stream with the measurement made on the reference sample.

6. The process of claim 4 wherein the step of introducing $SO_2$ into the sample stream to form a reference sample is accomplished periodically and wherein the steps of monitoring the absorbance of the sample stream and measuring the difference in the absorbance of the sample stream and reference sample are accomplished at different times at the same location.

7. The process of claim 3 further comprising the step of maintaining the pH of the process stream and the reference sample above about 10.0.

8. The process of claim 7 wherein the step of measuring the difference in the absorbance of the sample stream and the reference sample is accomplished at a wavelength of between about 330 and about 420 nm.

9. The process of claim 7 wherein the step of measuring the difference in the absorbance of the sample stream and the reference sample is accomplished at a wavelength of between about 350 and 380 nm.

* * * * *